United States Patent
Black et al.

(10) Patent No.: US 6,677,161 B2
(45) Date of Patent: Jan. 13, 2004

(54) AEROGELS AND OTHER COATINGS AS COLLECTION MEDIA AND MATRIX SUPPORTS FOR MALDI-MS APPLICATIONS

(75) Inventors: Eric Black, Charlottesville, VA (US); Charles E. Daitch, Charlottesville, VA (US); Wayne Bryden, Ellicott City, MD (US); Peter Scholl, Silver Spring, MD (US)

(73) Assignee: Veridian Erim International, Inc., Ann Arbor, MI (US)

( * ) Notice: Subject to any disclaimer, the term of this patent is extended or adjusted under 35 U.S.C. 154(b) by 199 days.

(21) Appl. No.: 09/975,487

(22) Filed: Oct. 10, 2001

(65) Prior Publication Data

US 2002/0081746 A1 Jun. 27, 2002

Related U.S. Application Data

(60) Provisional application No. 60/239,414, filed on Oct. 10, 2000.

(51) Int. Cl.[7] .............................................. G01N 24/00
(52) U.S. Cl. ...................... 436/173; 436/174; 436/178
(58) Field of Search .................................. 436/173, 174, 436/178

(56) References Cited

U.S. PATENT DOCUMENTS 5,777,325 A * 7/1998 Weinberger et al. ........ 250/287
5,808,300 A * 9/1998 Caprioli ...................... 250/288

FOREIGN PATENT DOCUMENTS

WO          WO 99/43743          *    9/1999

OTHER PUBLICATIONS

Chuck Daitch, "MALDI-MS Using Matrix-Doped Silica Aerogel Coated Tapes", Oct. 10, 2000, 6th International Symposium on Aerogels, Oct. 8–11, 2000, New Mexico, USA.*
Santos et al. "Optical properties of dye molecules adsorbed on fractal structures", Journal of Non-Crystalline Solids (1986), 82(1–3), 165–70 (Abstract).*

* cited by examiner

Primary Examiner—Jill Warden
Assistant Examiner—Yelena Gakh
(74) Attorney, Agent, or Firm—Gifford, Krass, Groh, Sprinkle, Anderson & Citkowski, PC

(57) ABSTRACT

Techniques to modify and apply aerogel coatings are described, including the application of spray-coated aerogels. The approach eliminates several of the wet chemical techniques previously needed for processes such as MALDI processing, and simplifies the automation of processes such as continuous monitoring in a sensor based format. With respect to MALDI processing, the preferred embodiment uses an acid-doped silica aerogel coated tape as the collection media as well as the matrix support. Although aerogels are disclosed as a preferred matrix material, other materials may alternatively be used, including linoleic acids, oleic acids, PEG (polyethylene glycol), preferably in tape format.

4 Claims, 3 Drawing Sheets

A

B

AEROGELS AND OTHER COATINGS AS COLLECTION MEDIA AND MATRIX SUPPORTS FOR MALDI-MS APPLICATIONS

REFERENCE TO RELATED APPLICATION

This application claims priority from U.S. Provisional Patent Application Ser. No. 60/239,414, filed Oct. 10, 2000, the entire contents of which are incorporated herein by reference.

FIELD OF THE INVENTION

This invention relates generally to molecular mass spectrometry and, in particular, to the use of aerogels and other coatings as collection media and matrix supports for MALDI-MS applications.

BACKGROUND OF THE INVENTION

Matrix Assisted Laser Desorption and Ionization Mass Spectrometry (MALDI-MS) is a method that yields repeatable and consistent mass spectra for molecules which tend to fragment easily and uncontrollably under harsh mass spectroscopy ionization methods. Softer ionization methods such as MALDI have recently been used to ionize and desorb intact biomolecules as large as 300,000 Daltons into the gas phase for mass analysis.

The basis of MALDI is the interaction of a pulsed laser beam with a laser desorbing matrix material into which analyte molecules are dispersed. Pulsed laser energy is absorbed by the matrix and transferred to the analyte, causing it to be ionized and desorbed into the gas phase. In the process, the analyte chemically interacts with the fragment ions of the matrix, forming molecular adduct ions.

The MALDI process typically involves wet chemistry techniques, whereby a solution of the matrix molecule is physically mixed with a solution containing the analyte. The resulting mixture is applied to a sample probe, allowed to dry, and introduced to the mass spectrometer for analysis. The current use of wet chemistry is one of the drawbacks of the process, in that multiple steps are required, certain of which are not conducive to automation.

SUMMARY OF THE INVENTION

This invention provides novel techniques to modify and apply aerogel coatings, including the application of spray-coated aerogels. This approach improves upon the existing art by eliminating several of the wet chemical techniques previously needed for processes such as MALDI processing, as well as simplifying automation for processes such as continuous monitoring in a sensor based format. With respect to MALDI processing, the preferred embodiment uses an acid-doped silica aerogel coated tape as the collection media as well as the matrix support.

The ability to pattern and apply aerogels to surfaces which may have previously been difficult to apply opens up new areas in which aerogel technologies may prove useful. The demonstration of using aerogel as a matrix to hold a variety of analytes in a tape format is novel as well. Although aerogels are disclosed as a preferred matrix material, other materials may alternatively be used, including linoleic acids, oleic acids, PEG (polyelthylene glycol), preferably in tape format.

DETAILED DESCRIPTION OF THE INVENTION

Before describing the preferred embodiments, the advantages of aerogels and aerogel-coated tapes will be discussed as they relate to the invention. First, aerogels offer a tremendous increase in surface area. Silicate species for the most part are biologically inert, which aids in the nondestructive transfer of the specimen from the collection/concentration area to the analysis area. The surface of the silica aerogel also has the ability to be functionalized with a variety of different compounds that may make collection more specific and/or more efficient. Furthermore, compounds that may make analysis easier and aid in analytical procedures may similarly be attached.

The use of aerogel coatings on a VHS tape format APL has the advantage of eliminating preparation steps prior to analysis in their instrument. The primary step which is eliminated is the application of MALDI matrix to the collected sample. This is a process that has been found to complicate automation, due to clogging of nozzles and unreliable amounts of material being deposited. Removal of this step improves automation in that only a small amount of solvent applied to the tape is needed to complete the processing between collection and analysis. It is also believed that the aerogel coating on the tape will increases the performance of the collector.

Experimental Procedures

The MALDI acid doped aerogel tapes were prepared using a dip-coating solution. The solution was prepared in accordance with the following procedure. A prepolymerized silicate mixture was synthesized by combining tetraethylorthosilicate (TEOS) with ethanol and water and dilute hydrochloric acid catalyst. This mixture was further polymerized under dilute conditions (ethanol solvent) using dilute ammonium hydroxide catalyst. When the polymerization had proceeded to the gel-point, the sample was washed with several solvent exchanges and silylated using trimethylchlorosilane. The appropriate MALDI acid was added to its saturation point and sonication was used to provide the final coating solution.

Dip coating was done using a Parker Compumotor microstepping apparatus which was set to pull a sample from solution at a specific rate. MALDI-aerogel dots were applied to tapes using a Paashe air-brush system set to spray several very dilute coatings in a layering process using a mask with the dot size and location.

Sample preparation for the MALDI-TOF-MS analysis involved taking the aerogel coated tapes and manually depositing samples of bioweapon simulants that were prepared by pipetting a solution of a known concentration to deliver the analyte to the sample surface. The samples were then treated with solvent (0.5 uL of 70% acetonitrile/30% water at 0.1% TFA). Multiple spots were done for each sample to ensure accurate responses. Analysis was done using the Kratos MALDI 4 TOF-MS system.

Results And Discussion

Figure 1:
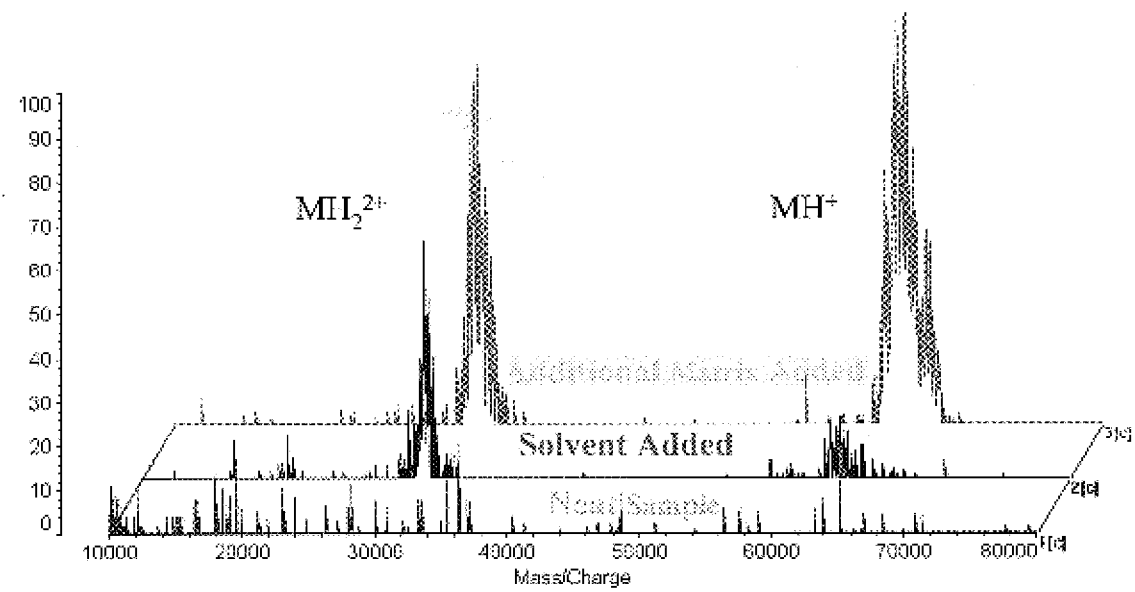
FIG. 1 demonstrates that characteristic spectra for Ricin D and SEB can be obtained by the simple addition of solvent to the aerogel and MALDI matrix coated tapes.
Figure 2:
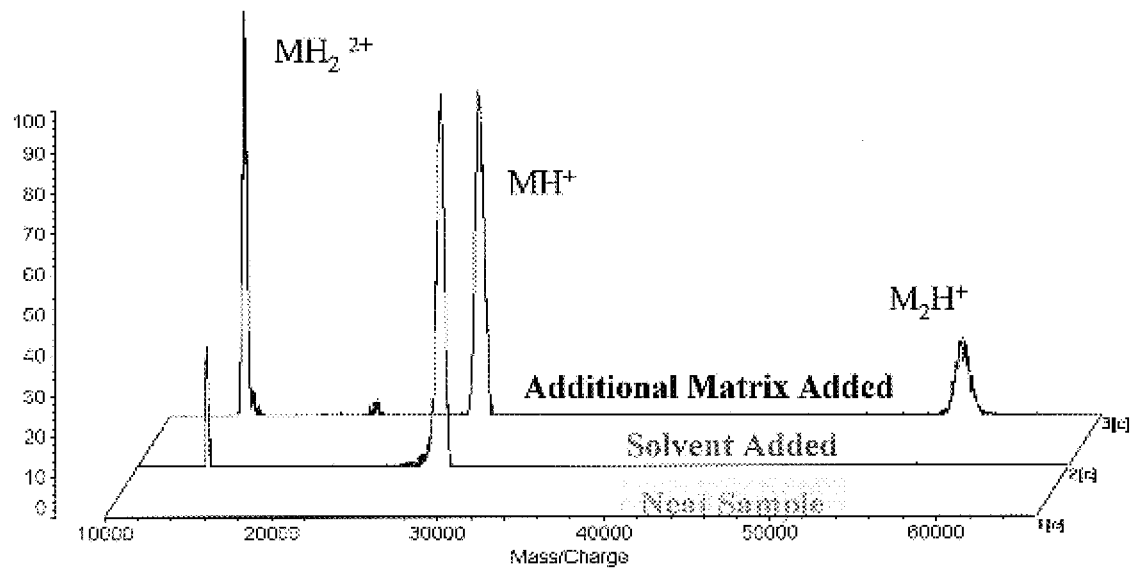
FIG. 2 is a different set of spectra obtained according to the invention.

Spectra attained from the procedures outlined above are shown in FIGS. 1 and 2. These spectra demonstrate that characteristic spectra for Ricin D and SEB can be obtained by the addition of solvent to the aerogel and MALDI matrix coated tapes. However, additional MALDI matrix improved the sensitivity of detection of MH+. This suggested more MALDI matrix should be doped into the aerogel substrate.

Figure 3A:
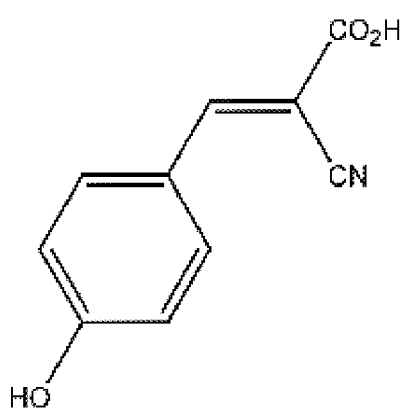
FIG. 3A illustrates an original MALDI acid precursor, namely, α-cyano-4-hydroxycinnamic acid (ACHCA) A.
Figure 3B:
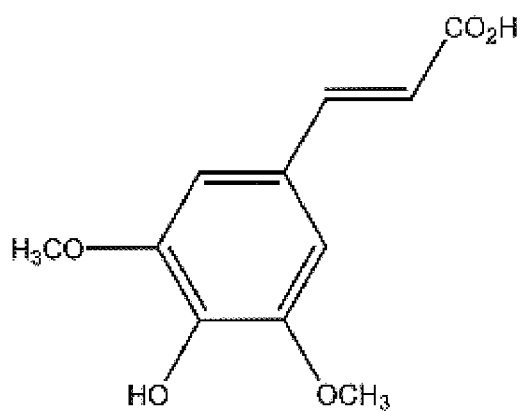
FIG. 3B illustrates a preferred MALDI matrix molecule, Sinapinic acid (SA) or 3,5-dimethoxy-4-hydroxycinnamic acid B.

The original MALDI acid precursor was α-cyano-4-hydroxycinnamic acid (ACHCA) A, shown in FIG. 3A. This molecule suffered from limited solubility in common organic solvents that were compatible with the sol-gel processes used to generate our dip-coating solutions. The experiments above were run using a new MALDI matrix molecule, Sinapinic acid (SA) or 3,5-dimethoxy-4-hydroxycinnamic acid B shown in FIG. 3B. The substitution of the new MALDI matrix material increased solubility 50% without the addition of tetrahydrofuran cosolvent which is necessary for (SA) A to maintain solubility throughout the application process.

Another problem encountered was the tape coatings interfering with the vacuum seal necessary for subsequent readings. The o-ring which provides the seal in the mass spectrometer was found to give the necessary vacuum on the first sample (1 uTorr), but due to aerogel sticking to the o-ring, subsequent samples gave unacceptable seals (6uTorr). Although recleaning and greasing the o-ring be problem, this is unacceptable during a continuous run.

This problem was solved by eliminating the complete covering of the tape by dip-coating and instead using aerogel spots on the tape which could be encompassed by the o-ring seal, yet still provide the benefits previously noted with the aerogel doped materials. To accomplish this, the aerogel was applied to the tape by a spray coating process using a mask which was designed to put the spots directly where the air collector deposited the sample and the mass spectrometer reads the sample.

To further explore the boundaries in which aerogel coatings can aid in sample analysis by Tiny-TOF, a study was initiated which examined the limits of detection for a variety of different molecular weight biological weapon simulants using matrix-doped aerogel tapes prepared a variety of different ways. The following variables were examined:

Comparison of using aerogel coated tapes vs using uncoated tapes or metal surfaces The effect of simulant molecular weight on signal and detection limit The effect of coating speed on tape loading and detection The effect of matrix loading level on detection To determine the effect of using an aerogel coating versus an uncoated tape or a metal surface, UV-Vis spectroscopy was used to determine the amount of matrix per unit area on the aerogel coated tapes. This was done in an effort to provide a fair test between the three methods as matrix loading would be expected to significantly affect the results. It was determined in the ACHCA coated tapes that the concentration of ACHCA $7.8 \times 10^{-7}$ M/cm$^2$. The SA coated tapes yielded a slightly smaller value of $5.3 \times 10^{-8\ M/cm2}$. This would seem to contradict the solubility data from above where a greater amount of SA is incorporated into the coating solution. The explanation for the smaller amount of SA is more than likely due to a difference in wetting ability between the two coatings solutions and a thinner coating thickness being obtained from the SA solution.

Figure 4:
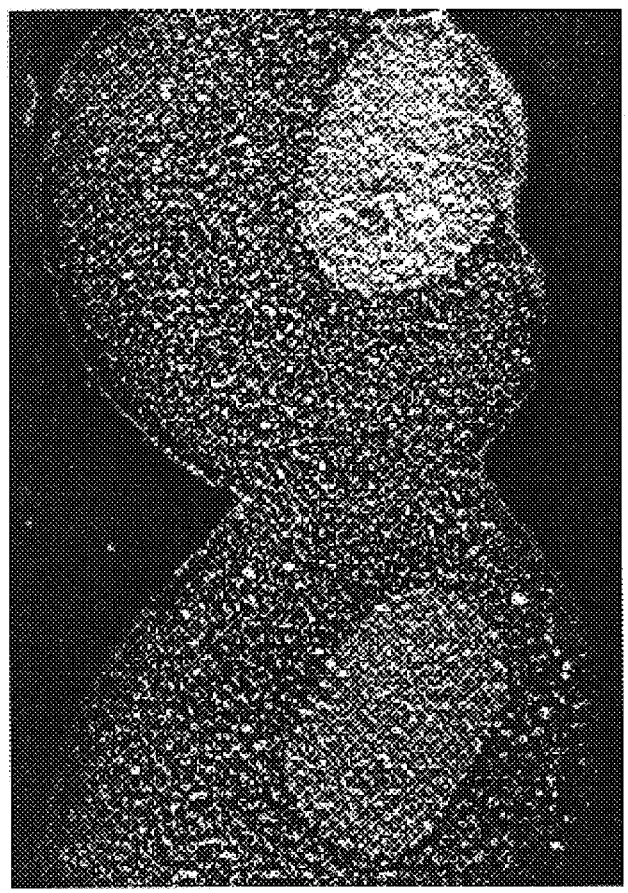
FIG. 4 is a photograph of two tape samples showing the analyte (inner ring) and solvent wash effect (outer ring)
Figure 5:
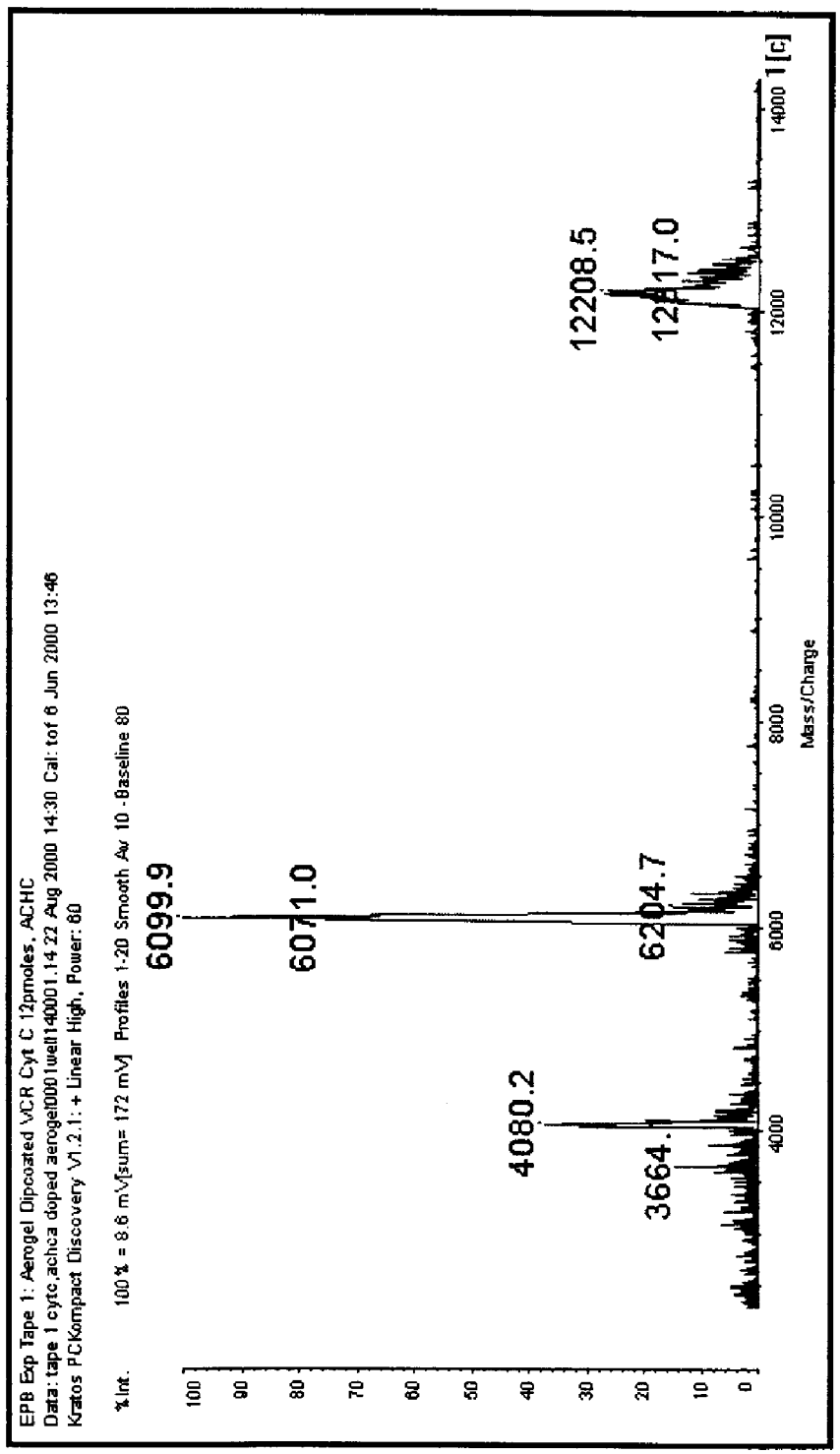
FIG. 5 is a spectra obtained using the sample of FIG. 4.

Remarkably when the amount of tape wetted by the analyte dose is taken into account, matrix:analyte concentration ratios using a typical analyte application (12 pmol) are found to be approximately 100:1 or less. Typical spectra are usually obtained at matrix to analyte concentration of 1000:1 or greater. Spectra for cytochrome C were easily obtained using tapes prepared with both matrix materials in the low concentration amounts. A photograph of two tape samples showing the analyte (inner ring) and solvent wash effect (outer ring) is shown in FIG. 4 and sample spectra is shown in FIG. 5.

MALDI-TOF-MS spectra of cytochrome C (Avg. MW 12384 kDa) were obtained through manual application on matrix-doped aerogel tape on a Kratos MALDI discovery using positive ionization, linear, high operation modes. Reproducing these results on blank tape and metal surfaces using the same concentration levels do not yield spectra until additional matrix is added to bring the level up to 1000:1.

The next experiment involved taking tapes that were doped at the 12 pmol levels mentioned above with BSA (MW 66000), ovalbumin (MW 45000), Substance P (MW 1347) and a low molecular weight polypeptide chain (arg-lys-asp-val-tyr, MW 679). The tapes were prepared so the ratio of matrix to analyte was 100:1 or less. The data obtained followed typical MALDI behavior with the exception of the unusually low ratio. SA is typically used for high molecular weight species and the samples equal to or higher in molecular weight than cytochrome C (MW 12300) gave spectra. The lower molecular weight samples were easily obtained by using ACHCA with the cutoff again being cytochrome C and no spectra being obtained for the higher molecular weight species with this matrix. Examples of these spectra are shown below.

MALDI-TOF-MS spectra were also obtained for bovine serum albumin (Avg. MW 66000 kDa), substance P (Avg. MW 1347 kDa), and a polypeptide chain (Avg. MW 679 kDa), each manually applied on matrix-doped aerogel tape on a Kratos MALDI discovery using positive ionization, linear, high operation modes. Only the ovalbumin failed to give a spectra up to this point. It is hypothesized that the preparation of only using water to solubilize the material resulted in clumping and another prep for these slides will be sought in the future. Limits of detection using the various molecular weight samples listed above were all around 1 pmol without exception. This level is similar to that for manually prepared samples using typical preparation procedures.

Using UV-Vis spectroscopy to determine the concentration of analyte on tapes which were prepared using different coating speeds showed that the amount of matrix did decrease as expected with lower coating speeds. This is expected as lower coating speeds yields thinner coatings. The spectra obtained showed that the previous test samples mentioned above are on the edge of the limit of detection for the amount of matrix they contain. The lesser amounts of matrix which resulted from the thinner coatings did not yield spectra for any of the analytes listed above (assuming that the coating thickness has no effect on the production of spectra).

We claim:

1. A method of MALDI-MS analysis, comprising the steps of providing a substrate applying an aerogel to at least a portion of the substrate introducing an analyte into the aerogel, thus creating a sample, and performing MALDI-MS analysis on the sample.

2. The method of claim 1, wherein the substrate is a tape.

3. The method of claim 2, further including the steps of covering of the tape through dip-coating containing an appropriate MALDI acid; and applying the aerogel to localized regions of the coated tape.

4. The method of claim 3, the aerogel is applied in localized regions of the tape through spray coating.

* * * * *

UNITED STATES PATENT AND TRADEMARK OFFICE
CERTIFICATE OF CORRECTION

PATENT NO.    : 6,677,161 B2
DATED         : January 13, 2004
INVENTOR(S)   : Erick Black et al.

It is certified that error appears in the above-identified patent and that said Letters Patent is hereby corrected as shown below:

Column 3,
Line 23, replace "o-ring be problem" with -- 0-ring between samples solved the problem, --.
Line 54, replace "- $5.3 \times 10^{-8M/cm2}$" with -- $5.3 \times 10^{-8} MC/cm^2$ --.

Column 4,
Line 52, replace "comprising" with -- comprising: --.
Lines 53 and 54, replace "substrate" with -- substrate, --.

Signed and Sealed this

Fifteenth Day of June, 2004

JON W. DUDAS
*Acting Director of the United States Patent and Trademark Office*